United States Patent [19]
Wright et al.

[11] Patent Number: 5,339,700
[45] Date of Patent: Aug. 23, 1994

[54] SAMPLE COLLECTOR

[75] Inventors: Paul G. Wright, Pleasant Dale; Frederick A. Nabity, Lincoln, both of Nebr.

[73] Assignee: Isco, Inc., Lincoln, Nebr.

[21] Appl. No.: 808,530

[22] Filed: Dec. 16, 1991

[51] Int. Cl.$^5$ .............................................. G01N 1/14
[52] U.S. Cl. .................................................. 73/864.34
[58] Field of Search .......... 73/863.02, 863.03, 863.83, 73/864.31, 864.34, 864.35, 864.91; 53/451, 551, 552, 570, 571

[56] References Cited

U.S. PATENT DOCUMENTS

| | | | |
|---|---|---|---|
| 3,453,799 | 7/1969 | Cloud et al. | 53/570 |
| 3,921,456 | 11/1975 | Newcomb, Jr. et al. | 73/863.02 |
| 4,265,074 | 5/1981 | Reuter et al. | 53/551 |
| 4,525,979 | 7/1985 | Lin et al. | 53/285 |
| 4,852,413 | 8/1989 | Niskin et al. | 73/864.63 |
| 4,860,836 | 8/1989 | Gunther | 73/153 |
| 4,945,713 | 8/1990 | Widenback | 53/570 |
| 4,998,621 | 3/1991 | Meehan | 53/449 |
| 5,036,001 | 7/1991 | Gork et al. | 73/864.24 |

Primary Examiner—Robert Raevis
Attorney, Agent, or Firm—Vincent L. Carney

[57] ABSTRACT

To draw samples of liquid for later analysis, liquid is periodically pumped from the inlet port in coordination with initiating movement of a web of packaging material, folding the package material and sealing it to form a pouch. The liquid is pumped from the inlet port into the pouch and the pouch is sealed. The pumping means and the equipment for drawing the web are controlled so that the container corresponds in internal volume to the volume of liquid pumped into the container prior to sealing the container and identification is printed onto the web becomes part of the package for the liquid.

20 Claims, 12 Drawing Sheets

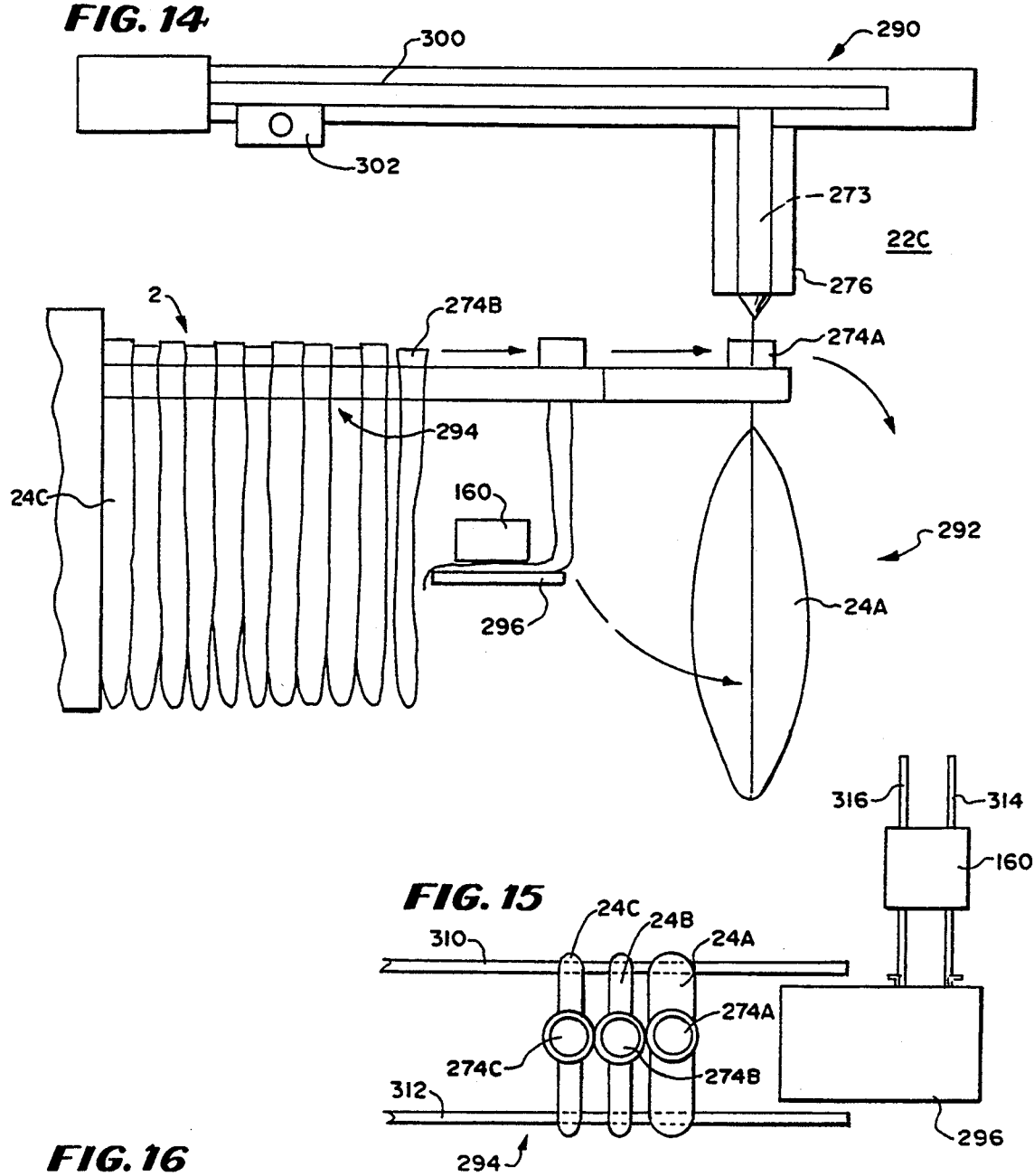
FIG. 14
FIG. 15
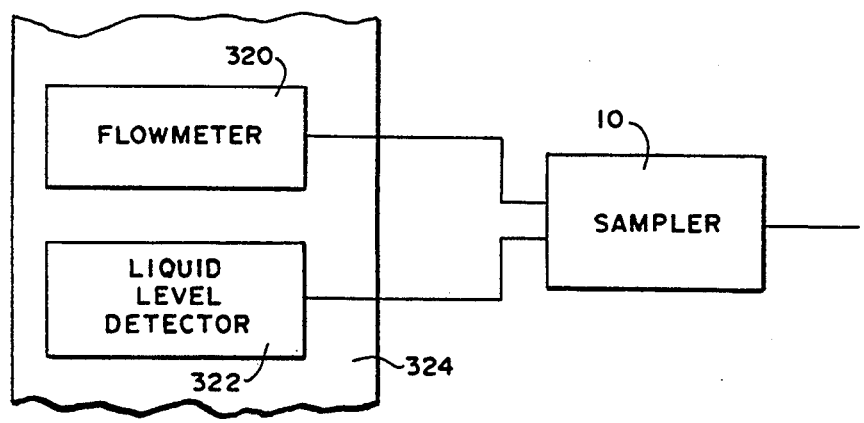
FIG. 16

SAMPLE COLLECTOR

BACKGROUND OF THE INVENTION

This invention relates to sample collectors, such as for example, sample collectors that periodically remove a specimen of waste water or well water and deposit it in a separate container for analysis.

In one class of sample collectors, a series of samples of water are pumped into an inlet and from the inlet to an outlet. At the outlet, the samples are deposited in separate containers for later analysis.

In a prior art type of sample collector of this class, the containers are bottles and the outlet and bottles are moved with respect to each other so that samples are deposited in different bottles for later analysis. The prior art sample collectors have several disadvantages, such as: (1) it is difficult to fill the containers completely; (2) it is difficult to seal the containers thus easily contaminating the liquid with gases in the air or from other sources; (3) it is difficult to adjust the apparatus to handle different size samples; and (4) the apparatus is subject to spillage caused by failure to register the container with the outlet or to match the amount of sample with the size of the container or other bottle.

SUMMARY OF THE INVENTION

Accordingly, it is an object of the invention to provide a novel sample collector.

It is a further object of the invention to provide a novel method for collecting samples.

It is a still further object of the invention to provide a novel sequential sampler for water.

It is a still further object of the invention to provide a novel method and apparatus for sealing samples of liquid to reduce contamination.

In accordance with the above and further objects of the invention, a computer periodically causes a packaging assembly to form an open package. In coordination therewith, a pump assembly begins to pump a sample so that the open container is in position and sealed at the bottom by the time the fluid flows from the outlet into the container inlet. The packaging assembly then seals the container relatively tightly and permits it to fall a short distance as a sealed package containing one or more samples. Preferably, the web material is printed with: (1) an identification number; (2) a sequence number; (3) time of sample; (4) reason for sample initiation (e.g. time setting, external trigger, etc); and (5) volume of sample; as the package is being formed in a manner known in the art.

In one embodiment, the package is formed of continuous web material. In other embodiments, they are formed of tubular web material in the packaging assembly or are separately formed in one packaging machine and utilized in another that fills them with samples, such as through a large diameter needle introduced temporarily into the package through a septum. The packages may be cut after they are sealed into separate packages before the next package is sealed or may be formed as a continuous series of separated compartments that are interconnected by web material. Each package or compartment may contain one sample drawn at one time or a plurality of samples drawn at different times.

In use, the samples are moved with printed identification on them to a source of analysis. At that source, analysis is performed using the printed information on the package. For example, the printed information may indicate the source of the samples, the volume of sample in the package, the cause of the initiation of taking a sample, such as for example, was it at periodic time settings or externally triggered or manually triggered or the like.

In one mode of analysis, at the laboratory receiving the packages, a determination is made of the tests that are to be performed and the volume needed for each test. A configuration of tests may then be made up which utilizes the volume most efficiently by dividing the volume needed for each test into the total volume of the package. In this way, maximum benefit can be obtained from the given volume as indicated on the package.

The time the sample is taken also provides useful information. For example, in some industrial uses, tests are performed for toxic contaminants such as chromium or arsenic in a plating facility. The detection of such a contaminant and the time at which it occurs enables the testor to analyze the source of leakage of the contaminant into the fluid supply.

The sample initiation may indicate when a substance has been released into the system. This is more likely to be significant in an open channel sewerage system or the like where it is necessary to determine who has released a certain material for cost assessment purposes or the like. Thus, a change in the flow rate of the system or the level of the liquid as detected by a detector, may indicate the time during which the material is released into the system and thus provide an indication that a sample should be taken or a larger than usual sample should be taken.

As can be understood from the above description, the fluid sampler of this invention has several advantages, such as: (1) it can form a large number of packages; (2) data is conveniently printed right on the package as it is formed; (3) the size of the package can be automatically tailored to the size of the sample to avoid air that may contaminate the liquid therein; (4) the sample is immediately sealed in the package and thus reduces contamination; and (5) overflow can easily be avoided.

SUMMARY OF THE DRAWINGS

The above noted and other features of the invention will be better understood from the following detailed description when considered with reference to the accompanying drawings, in which:

FIG. 14 is a schematic elevational view of still another embodiment of web processing system;

FIG. 15 is a simplified plan view of the embodiment of FIG. 14; and

FIG. 16 is a block diagram showing a manner in which remote initiating systems may be connected cooperatively to the sampler.

DETAILED DESCRIPTION

Figure 1:
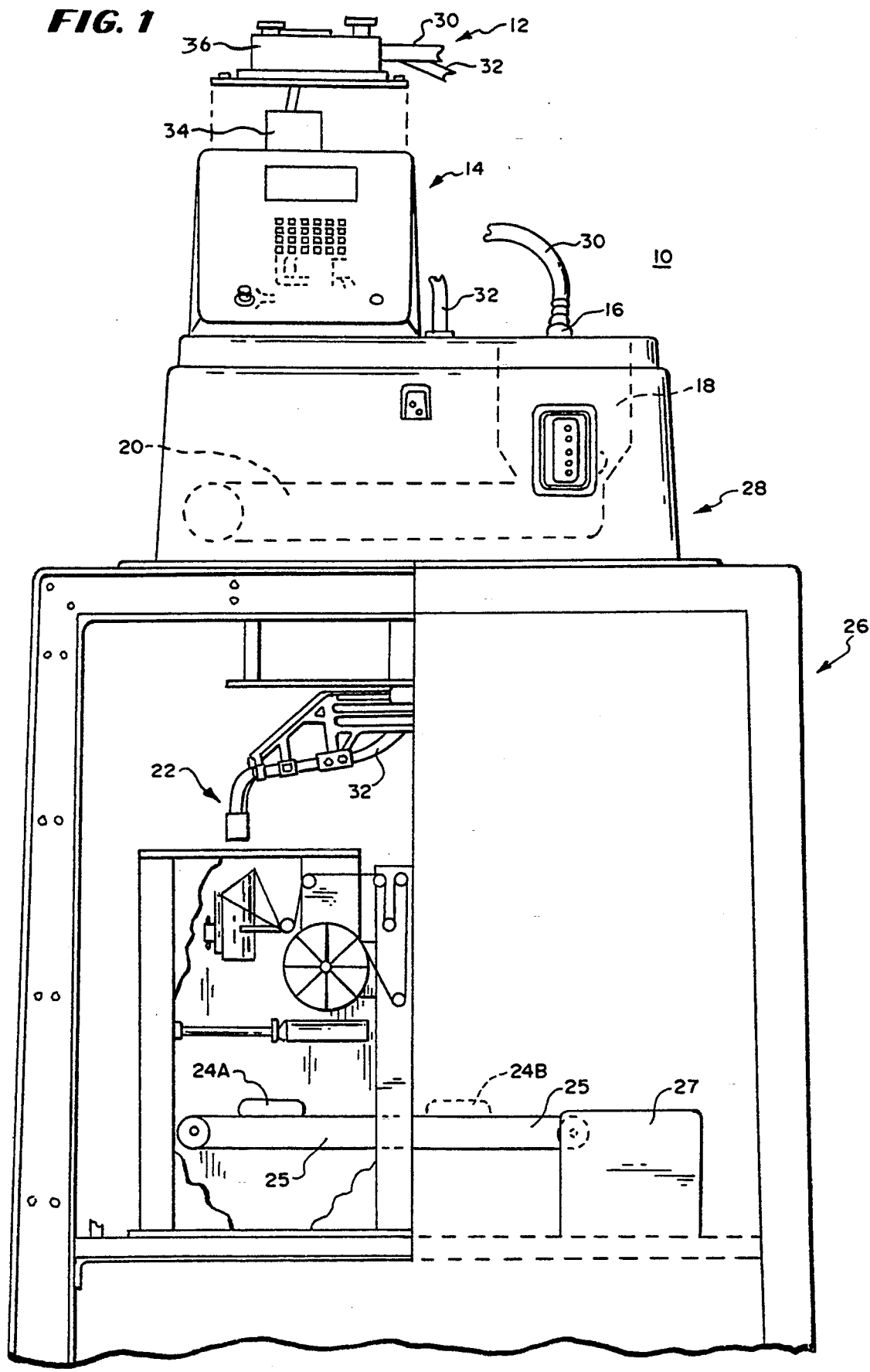
FIG. 1 is a fragmentary, elevational view, partly exploded, of the sampler which is an embodiment of the invention.

In FIG. 1, there is shown a fragmentary elevational view, partly exploded, of a sampler 10 having a pump assembly 12, a computer 14, an intake nozzle 16, a flow-through-channel 18, a front horizontal portion 20 of the wastewater pipe and a sample packaging assembly 22. Wastewater flows through the wastewater pipe and through the flow-through-channel 18 in a continuous flow. During the flow, the computer 14 measures periods of time and activates the pump assembly 12 at preset intervals of time or amounts of wastewater flow to draw samples of predetermined amounts of wastewater.

During the drawing of a sample, the pump pumps at a predetermined rate set to be approximately the rate of flow of the wastewater through the front horizontal portion 20. During this pumping action, the pump pumps wastewater: (1) from the flow-through-channel 18; (2) through the intake nozzle 16 which is inserted into the flow-through-channel 18; (3) through the hose sections 30 and 32; and (4) to the sample packaging assembly 22 which packages it, with one or more samples being totally enclosed in a different sample container such as containers 24A or 24B and moves the samples on a conveyer 25 to a storage container 27.

To provide pumping, the pump assembly 12 includes a peristaltic portion 36 having rollers which receive tubing: (1) a fluid inlet, a portion of which is indicated at 30; and (2) a fluid outlet, a portion of which is indicated at 32. The rollers are driven against a section of hose in a conventional manner by a motor 34 which is energized under the control of the computer 14.

The computer 14 counts revolutions of the peristaltic pump to monitor the purging of liquid from the tubing, starts the formation of a container, pumps a fixed amount of sample into each of the containers, such as the containers 24A and 24B through the hose sections 30 and 32, seals the containers in the sample packaging section 22, cuts the bags so that they drop a short distance onto the conveyer belt 25 and transports the containers on the conveyer belt to the storage container 27. This cycle is repeated for each new sample.

Because the sampler 10 is computer-controlled, samples may be drawn to fit in an individual bag, which may be air tight or may have surplus room, or samples may be periodically drawn with several samples at different time periods being poured into the same bag before it is sealed. The printing mechanism may indicate the nature of the samples in the bag. In this manner, the samples within one bag may be representative of the sampled liquid at one point in time and this is indicated on the bag, or in the case of composite or multiplexed sampling, the liquid in a bag may represent an average of the liquid taken at different time and this is indicated on the bag.

Figure 2:
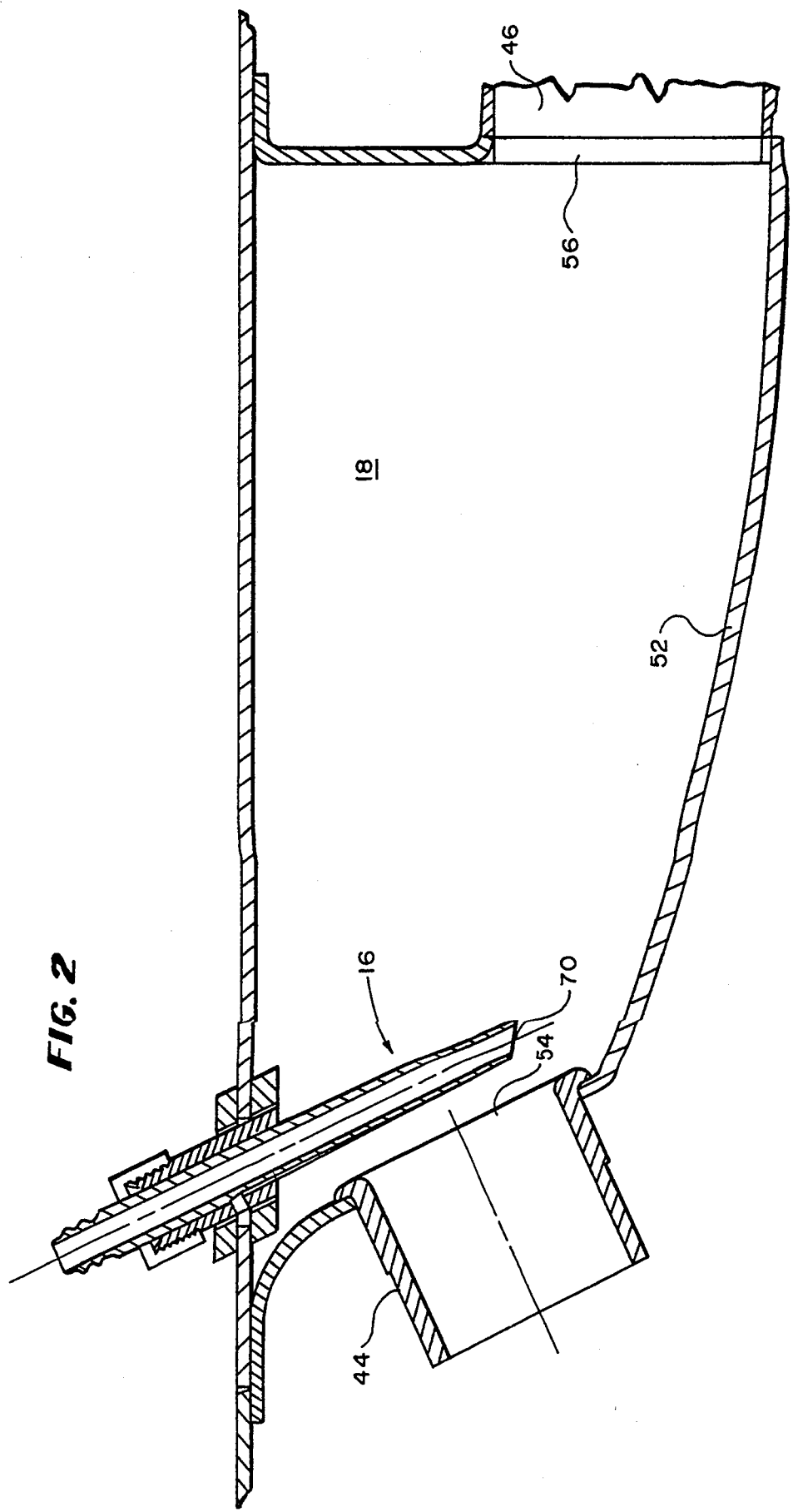
FIG. 2 is a sectional view illustrating a flow-through-chamber that is part of the embodiment of FIG. 1.

In FIG. 2, there is shown a sectional view of the flow-through-chamber 18 having a portion of the intake nozzle 16, an inlet port 54, an upwardly extending pipe member 44, an outlet port 56, and an outlet pipe 46. The flow stream being sampled is connected to pipe 44, flows through chamber 18 and out of pipe 46. The pump assembly 12 (FIG. 1) draws samples of liquid through the nozzle 16 and channels it into the packaging assembly 22 (FIG. 1) under the control of the computer 14 (FIG. 1).

Figure 3:
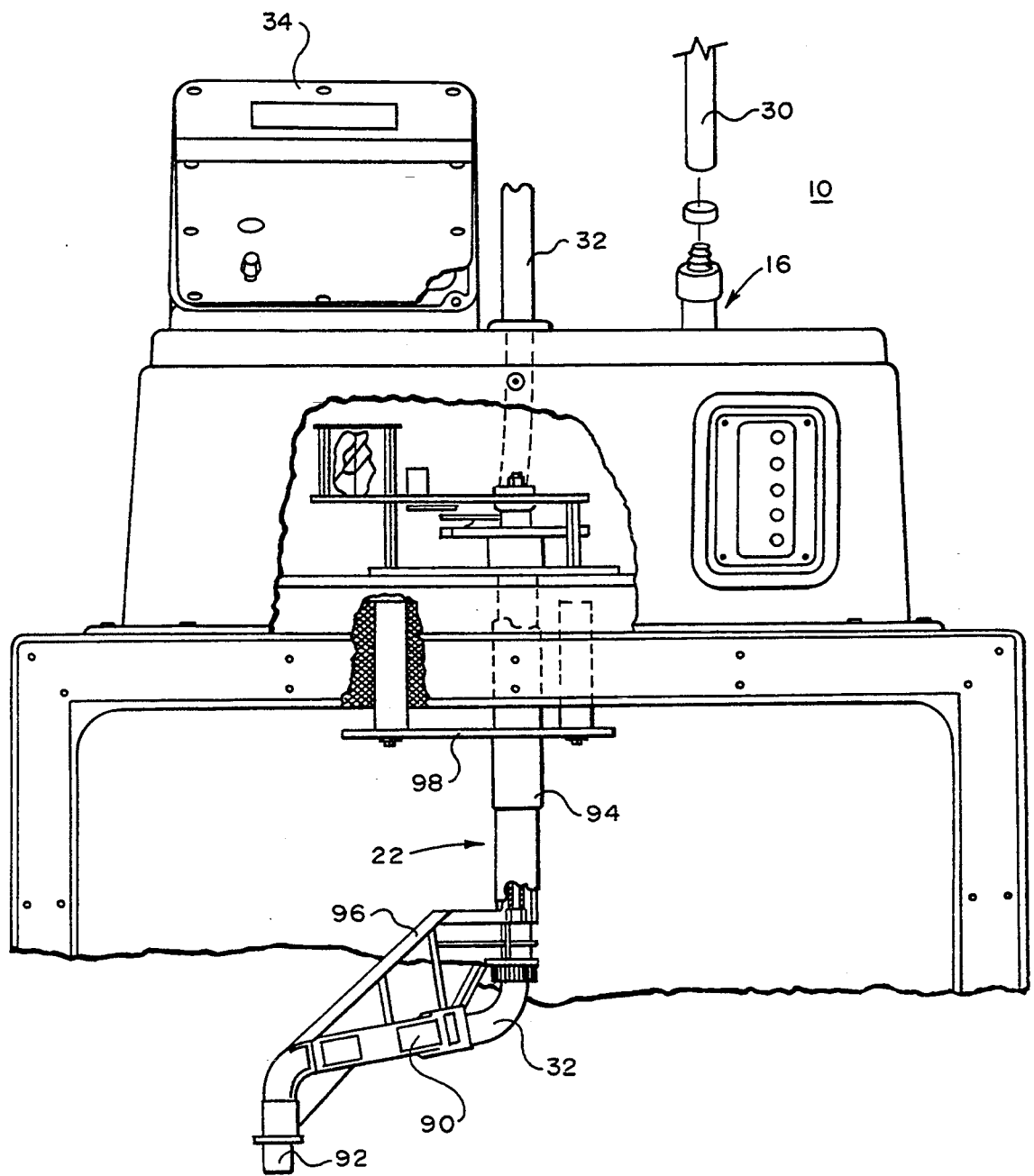
FIG. 3 is a fragmentary, elevational view, partly broken away and partly exploded, of an embodiment of an outlet for samples useful in the embodiment of FIG. 1.

In FIG. 3, there is shown a broken away, fragmentary, elevational view of the flow through sampler 10 showing the manner in which the hose 32 from the pump assembly 12 extends downwardly from the pump assembly 12 (FIG. 1) to an outlet arm 96 of the packaging assembly 22. The outlet arm 96 receives the hose 32 and supports it through an offset portion 90 and a downwardly extending portion 92. The hose 32 is held in this position by the outlet arm 96.

Figure 4:
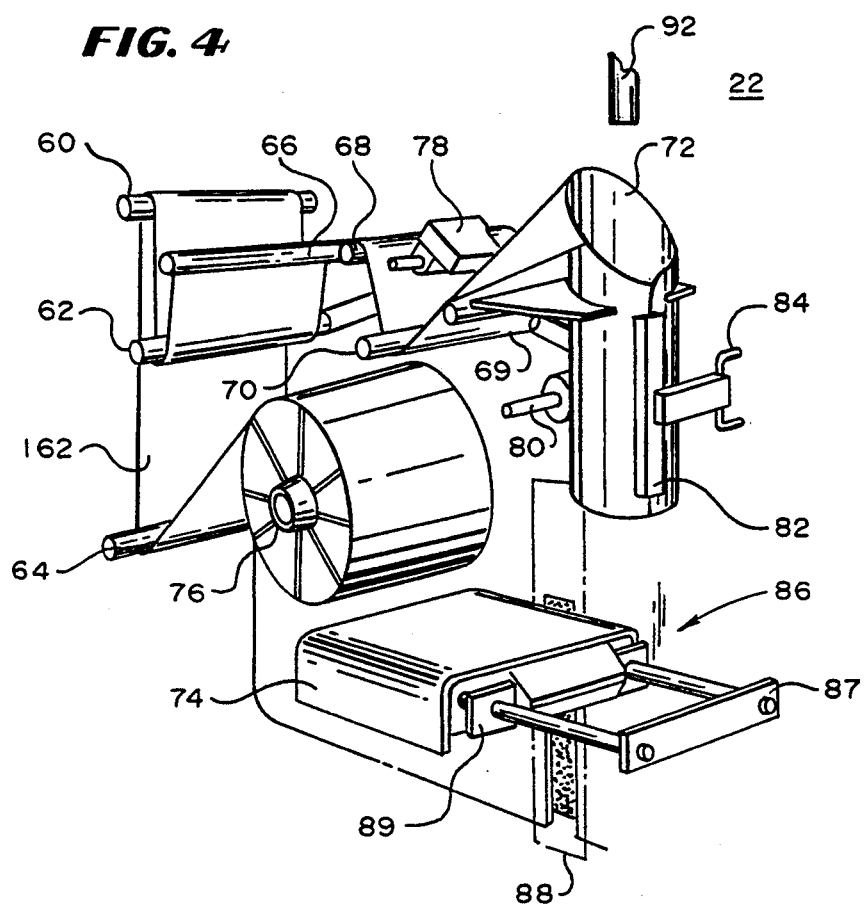
FIG. 4 is a fragmentary, perspective view of a web processing system that is part of the embodiment of FIG. 1.
Figure 5:
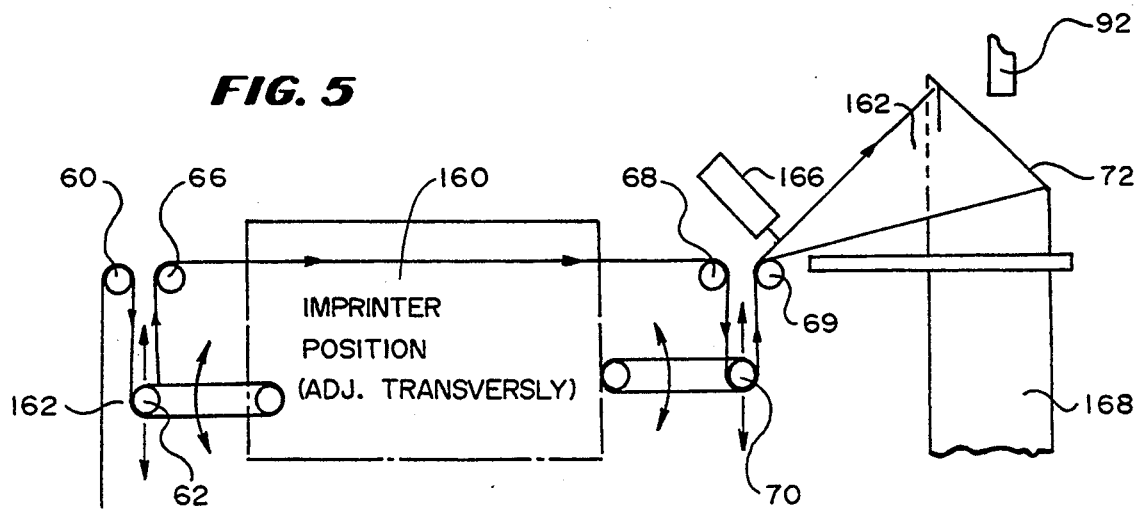
FIG. 5 is a schematic sketch of the web travel path of the embodiment of FIG. 4.

In FIGS. 4 and 5, there is shown a packaging assembly system 22 having a plurality of cantilevered rollers 60, 62, 64, 66, 68 and 70, a web folding assembly and water entry tube or chute 72 and a reciprocating end seal carriage 74 which provides the sole web transmit motive power. With this arrangement, a continuous web is unwound from the web roll 76 about the tensioning, braking, unwinding and dancing roller mechanism 64.

The movable registration roller 70 can change the length of the web 162 in the travel path and can serve with photodetectors 78 or the like to register pre-printed patterns for an updated printing code entry for example. These are necessary, particularly when changes in package length need to be made. Also, when new rolls 76 are inserted, automatic registration can be effected with pre-printed patterns on the web 162. Chute 72 may be changed if desired, by sliding onto shaft 80 to conform to different web and package widths and different package lengths.

Two layers of the web 162 are sealed longitudinally together by the pivoted heat-seal brake member 82 which pivots about a member 84. The heater therein is just hot enough to seal together two web layers but not to burn the web, so that it is not critical in length of contact time.

The web 162 is advanced by the lateral heat seal and clamping mechanism 86 which reciprocates such as by vertical movement in slot 88 to close and grab the web 162 at its uppermost position and to open and release it at the lowermost position, thereby grabbing and yanking a proper web length from web roll 76 while sealing the web laterally with a heated bar as it travels either during the downward stroke or/and as it rests in an upper position before movement for sealing before liquid flows into chute 72. Heat-seal 82 acts as a brake member to keep the web 162 from reverse movement when engaged. It is pivoted away from the web at pivot member 84 permitting it to move through the web path in timing with the carriage 74. The detailed operation of suitable clamping and sealing mechanism is set forth in U.S. Pat. Nos. 3,054,236, 3,067,555, 3,579,404, 4,262,470, 4,262,474 and 4,265,074 incorporated by reference herein.

Thus, the roller 64 engages web 162 and rotates web roll 76 counterclockwise to meter out an appropriate length of web 162 to form a package as the dancing roller 64 pivots downwardly. The length of the pivoted dancing roller arm and weight of the roller 64 can be varied to fit different web conditions.

The web travel path operating in conjunction therewith is simple to provide for easy threading over rollers 60, 62, 64, 66, 68 and 70. Adjustable roller 70 can permit registration of pre-printed patterns on web 162 with an imprinter 160 (FIG. 5) for coding a package. Similarly, registration roller 70 can adjust the registration of a pattern with the longitudinal brake member 82. Both registration rollers 68 and 70 can be swerved for automatic alignment in response to photo detectors 78 or the like.

In operation, the web 162 is hand-threaded without necessitating any power cycle or operation through a machine cycle to pull the web 162 into place. Thus, the web 162 is passed over web folding assembly 72 and vertically dropped into heat seal and clamping mechanism 86 where it is thereafter grasped between horizontally movable jaw 87 and jaw 89 for a machine operation. Instead of a clamping mechanish 86, the carriage 74 may contain a series of clips that clip the ends of the web tube shut and remain with the formed package. In such an embodiment, a hairpin clip is inserted by the force of the claiming member 87 over the end of the tube to form the seals.

Figure 6:
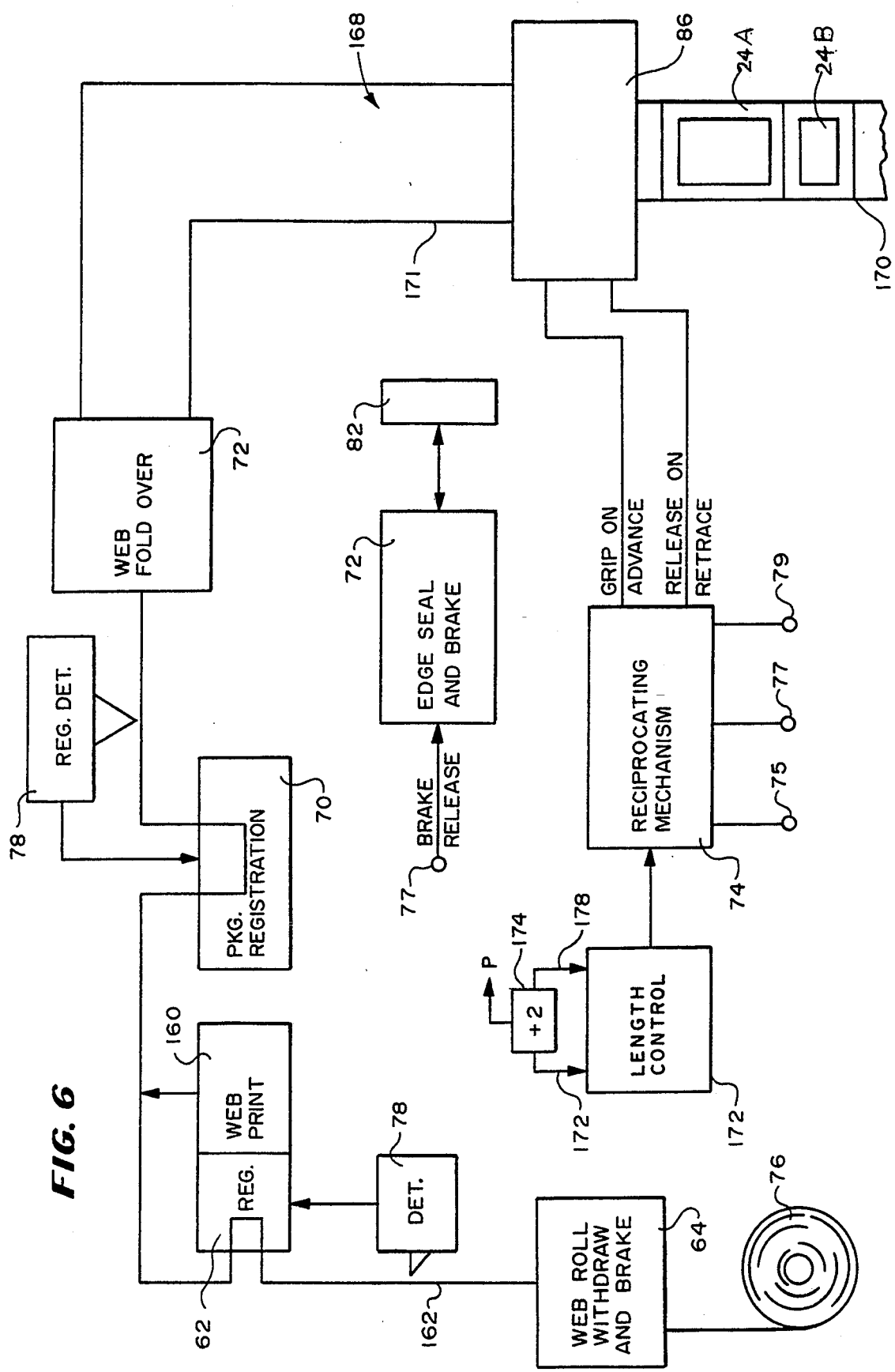
FIG. 6 is a schematic control diagram of the operation of the embodiment of FIG. 4.

In FIG. 6, there is shown a block diagram of the control circuits and interrelated mechanisms that control the operation of the liquid packaging system 22 (FIG. 1). As shown in this block diagram, the packaging system is triggered by a package forming command applied at 75 for advancing the web and forming a package to receive the sample. Thus, the command signal 75 is derived to trigger a web withdrawal cycle by actuating reciprocating mechanism 74 to pull the web from roll 76 and transversely end/seal the folded over web portion 168 after it is edge-sealed longitudinally by element 82.

As the transit device 86 grabs, seals and advances the web 168, an advance signal 77 is generated to release the edge seal and brake member 82 at web folding 72, permitting the web to be pulled from roll 76. The heat seal and clamping mechanism 86 exerts tension on web 162 but does not unroll a heavy web roll. The heat seal and clamping mechanism 86 raises the web dancing roller-brake assembly 64 as hereinbefore described so that the web is not unduly stretched or broken by acceleration of the heat seal and clamping mechanism 86 which draws a new length of web through the feed path. A similar signal 79 can be generated if desired in the system for auxiliary controls that need occur on the release and retrace the stroke of heat seal and clamping mechanism 86.

The web package is sealed along the container bottom edges 170 and the signal to terminal 75 is inhibited so that the web is stationary and braked while the seal member 82 seals the web longitudinally along an edge 171 upon receiving a retrace period signal on terminal 79. A transverse package seal is made by heat seal and clamping mechanism 86 as it clamps and holds the folded over edge sealed web 168. Finally, a signal causes pumping through a purge operation and pumps a sample into the web package. The package is then moved downwardly and sealed at the top.

Thus, by clamping and/or sealing, the liquid sample is retained in the package until a transverse seal at the top completes the package. For example, two sequential packages 24A, 24B on an uncut web may be formed with lateral seals to form bottom edges 170 therebetween, and the web can be cut near the edges 170, for example, to produce packages 24A and 24B.

Figure 7:
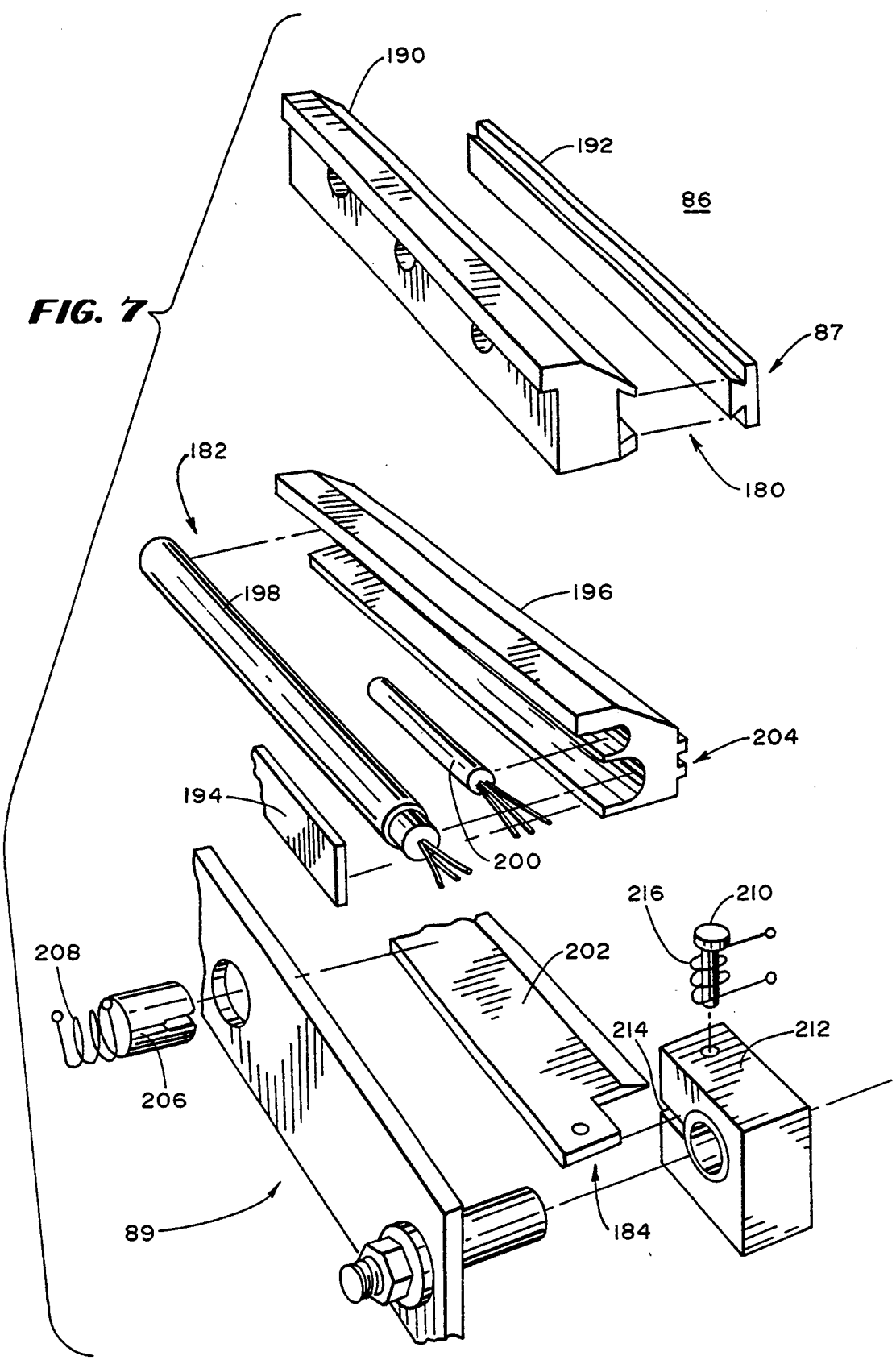
FIG. 7 is an exploded perspective drawing of a sealing device used in the embodiment of FIG. 1.

In FIG. 7, there are shown a series of devices attached to the heat seal and clamping mechanism 86 for engaging the web and processing it in the package forming and filling operation. Typically, a cold grasping assembly 180, a heat sealing assembly 182 and a programmable knife cutting assembly 184 are spaced along the length of the web and transversely extend across the web width. Other devices such as a perforating cutter that forms a tear line between two packages without severing the strip can also be used, as desired.

In operation, the cold jaw inserts 190 and 192, attachable to jaw 87, provide respectively a holder and a clamp with an elastic face that engages the opposite jaw assembly to grasp the web. These parts interfit by the tongue and groove assembly shown so that a new rubber facing can be easily installed without disassembly. Thus, this cold grasping assembly 180 closes the web tubing at the bottom of a package to be formed so that it can be filled with samples, while the devices 182 and 184, respectively, seal and cut the web. Other combinations and devices could, of course, be used on the jaws.

The heat seal assembly 182 stacks an insulator plate 194 and a heated metallic unit 196 into which is inserted in the receptacle grooves a heater element 198 controlled by a thermostat system operated by the heating detecting thermistor insert 200 located inside the receptacle jaw facing unit 196. Thus, the recepticle jaw facing unit 196 is heated to the proper temperature to press bead (or beads) 204 against the tubular web and seal the two layers together transversely at a location between successive packages.

The cutter assembly 184 has the knife blade 202 moving selectively into cutting position against an anvil (not shown) on the opposite jaw 87 by means of movable drive pin 206 which is programmed by the automated system and moves longitudinally to engage knife 202 and push it forward to cut the web at a position located between two adjacent packages.

If the drive pin is controlled by a solenoid or hydraulic cylinder, the drive pin can be intermittently controlled at the times desired. However, if cyclically driven during each package forming cycle by a cam or the like, it is provided with an intermediate compressible spring assembly 208 so that it can proceed over the cycle even if the knife blade is stopped short of the cutting position by inserting pin 210 in the block 212. The blade 202 is stopped short of the cutting anvil because pin 210 hits the blade on entry to slot 214 and thus holds it away from the cutting position to skip a cutting cycle whenever programmed by the accompanying system to operate solenoid coil 216 or some equivalent mechanism as a cam-operated interposer. The solenoid coil 216 is used to selectively control the cutting cycle in the process of providing strips of two or more adjacent packages.

The heat seal and clamping mechanism 86 is moved upwardly where the jaws can be closed to grip the web by means of cold grasping assembly 180 thereby closing the web tubing and permitting entry of a sample in chute 72 for forming a package to hold the sample. As the jaws move downwardly and pull a corresponding length of web from the roll 76, there is time to heat seal and cut the web to form a separate sample unit by cutting at the top of the preceding bag. A similar heat sealing assembly 182 may be located on the heat seal and clamping mechanism 86 beneath the knife 202, if desired, to seal the top of the preceding bag, which is released when the jaws open to drop vertically into a bin or on a conveyor belt.

Figure 8:
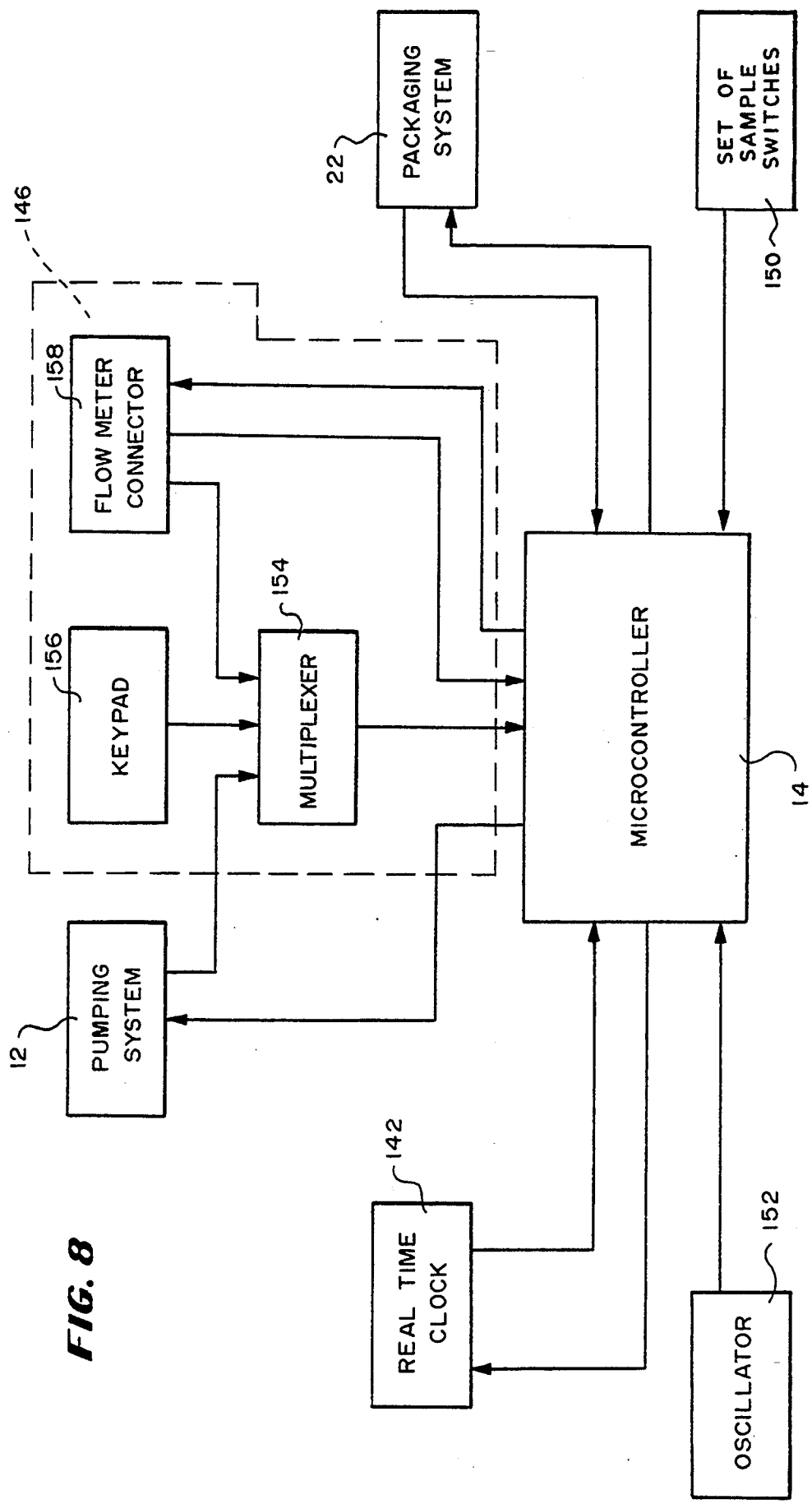
FIG. 8 is a block diagram of a control system for the sampler.

In FIG. 8, there is shown a block diagram of the microprocessor control system used in the preferred embodiment having the microcontroller or computer 14, the pumping system 12, a real time clock 142, an input interface 146, a packaging system 22 and a set of sample switches 150. The microcontroller 14 is a Motorola MC68HC705C8P microcontroller sold by Motorola, Inc., Microprocessor Products Group, Microcontroller Division, Oak Hill, Tex.

To control the wastewater sampler, an external oscillator 152 is connected to the microcontroller 14 in a conventional manner to establish a basic clock rate. The microcontroller receives signals from the real time clock 142 and from the input interface 146 to which it is electrically connected. The real time clock 142 provides presetable periodic signals to the microcontroller 14. Their signals are used to time events such as the drawing of samples or the like. The real time clock 142 periodically applies signals to the microcontroller 14 and is powered by a separate source of power such as a lithium battery which enables it to continue sending coded pulses that indicate the real time. It receives a signal from the microcontroller 14 upon initialization which sets the real time into the real time clock 142 so that it may provide accurate indications of time to the microcontroller 14.

The microcontroller 14, if it loses power, inquires of the real time clock 142 about the actual time upon receiving power to reset its registers. The real time clock also receives signals from the microcontroller 14 as to the duration of periodic intervals between signals to be sent by the real time clock 142 to the microprocessor 14 for timing events such as the drawing of samples or the like as preprogrammed into the microcontroller 14 through the user interface. For programming and timing some events, the input interface 146 includes: (1) a flow meter connector 158; and (2) a keypad 156 and a display that permits an operator to set the parameters such as the amount of flow between samples or the like.

The flow meter connector 158 may be electrically connected to a flow meter that provides a measure of wastewater flowing through the wastewater pipe or other stream that is being sampled. The signals from the flow meter may be utilized to cause a sample to be drawn at periodic intervals in coordination with the formation of a package to hold the sample and marking of the package.

To prevent an improper package size for a sample, the packaging system 22 adjusts the length of web before sealing and cutting under the control of the microcontroller 14 when the microcontroller 14 determines that the container into which it is depositing samples is full from a calculation based on the number of samples and the volume of each sample. It may then cause the packaging system to begin depositing samples into the newly formed packages and cutting them or allowing them to remain attached. The microcontroller 14 may be programmed to make this change at any selected volume of sample.

The sample switches sense the presence of containers 24A or 24B (FIGS. 1 and 6) and apply the signal to the microcontroller 14 indicating the presence or absence of the container. With this arrangement, the microcontroller 14 senses the presence of at least one of the containers 24A and 24B before it begins to signal a new cycle to form a package and start the pump assembly to fill the new package.

To control the pumping intervals, the microcontroller 14 may be programmed through the user interface to initiate pumping action from the pumping system 12 at intervals which occur after a predetermined amount of time or after a predetermined amount of flow as set through the user interface. The microcontroller 14 also has programmed into it the number of pumping cycles from the pumping system 12 for a continuous sample and the volume of the wastewater that is to be applied to the container 24A or 24B (FIGS. 1 and 6) before signaling the packaging system 22 to move to a new container, provided the sample switches 150 indicate that the former container is processed.

The pumping system 12 is also connected to the user interface which contains a multiplexer 154 and transmits signals thereto indicating the number of pump cycles. These signals are applied to the microcontroller 14 to count the wastewater which has been drawn either as a sample or to be pumped upwardly to a fixed location and downwardly to clear the line and to control the size of container.

The input interface 146 includes a multiplex unit 154 which is electrically connected to the keypad 156, the flow meter connector 158 and an output conductor from the pumping system 12. It periodically scans these units and sends signals to the microprocessor indicating the amount of sample drawn by the pumping system 12 or input programming from the keypad or control signals from the keypad 156 of flow volume values from a flow meter connected to the flow meter connector 158. The flow meter connector 158 also receives: (1) event signals from the microcontroller 14 for marking the web or the like connected to the flow meter or internal to the flow meter; and (2) signals from a separate detector or wastewater in the pipe or channel to signal the microcontroller 14 to indicate the presence or absence of flow through the wastewater pipe or channel.

Figure 9:
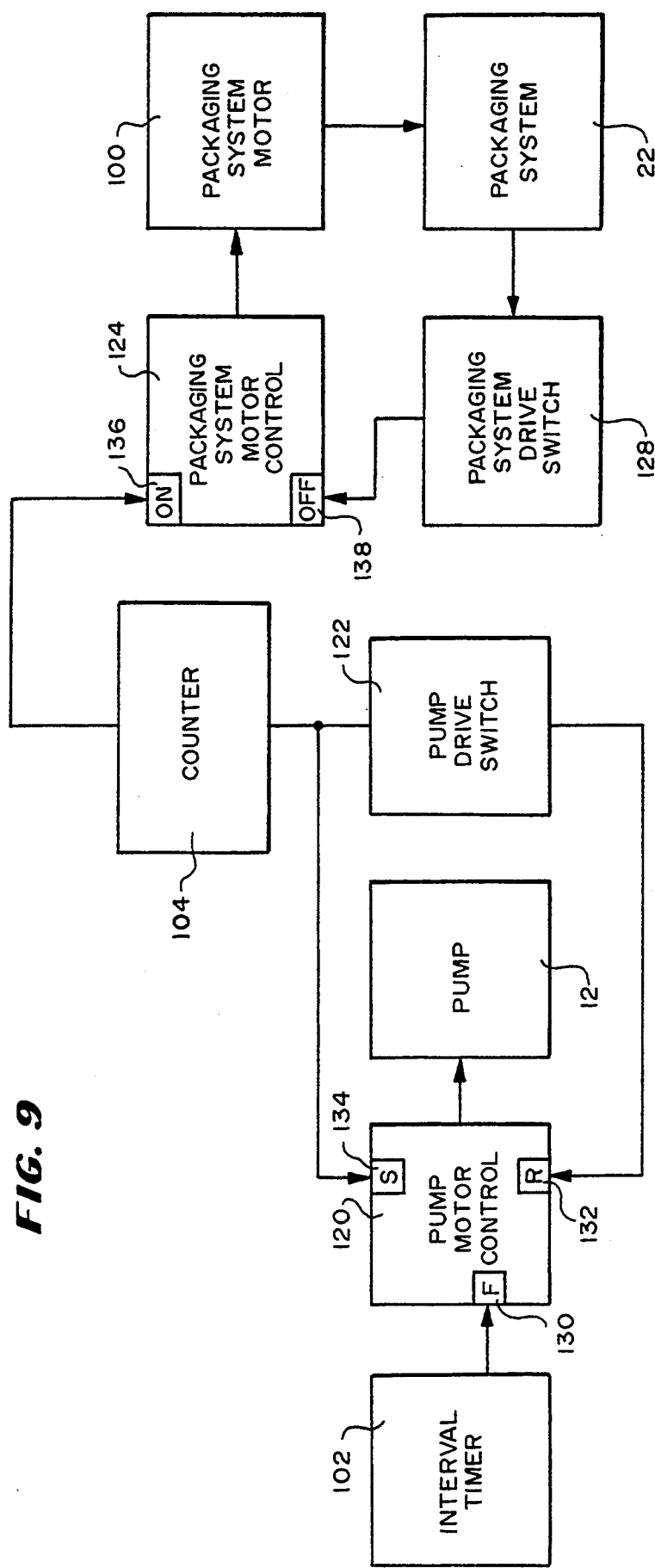
FIG. 9 is a schematic illustrative diagram of a hard wired version of the wastewater sampler.

In FIG. 9, there is shown a block diagram of a hardware control system which performs the functions which, in the preferred embodiment, are performed by the Motorola Microcontroller Model MC68HC705C8P and is available from Motorola, Inc., Microprocesssor Products Group, Microcontroller Division, Oak Hill, Tex. The controller system shown in FIG. 9 includes an interval timer 102, a ring counter 104, a pump motor control 120, the pump assembly 12, a pump drive switch 122, a packaging system motor control 124, a packaging system motor 100, packaging system 22 and the packaging system drive switch 128.

To start, stop and control the direction of rotation of the pump assembly 12, the pump motor control 120 includes a switching arrangement having: (1) a first position into which it is switched by a signal from the interval timer 102 to the forward drive terminal 130 of the pump motor control 120 and in which position it applies power to the pump assembly 12 in a direction that causes the pump assembly 12 to draw fluid into the intake hose 30 (FIG. 1); (2) a second position into which it is switched by a signal from the pump drive switch 122 to the reverse drive terminal 132 and in which position it stops the pump assembly 12 and applies power to the pump assembly 12 in a direction that causes the pump assembly 12 to force fluid out of the inlet of the intake hose 30 to clear the hose of fluid before another sample is taken; and (3) a third position into which it is switched by a signal from the pump drive switch 122 to the stop terminal 134 and in which position it stops the pump assembly 12. This signal is also applied to the adjustable ring counter 104 which has its selectable output terminal connected: (1) to the terminal 136 of the packaging motor control 124 to start the formation of a package by pulling the web to form a tube and sealing the bottom and side; and (2) to its own reset terminal to permit another count cycle.

To generate the signals that are applied to the reverse input terminal 132, the stop terminal 134 and the counter 104 input terminal, the pump drive switch 122 includes a cam-operated, revolution-sensing switch that is controlled by the rotation of the pump motor and a stepping switch that counts operations of the cam-operated revolution-sensing switch. The stepping switch produces a contact closure to provide a signal to the reverse input terminal 132 of the pump motor control 120 when the pump assembly 12 has rotated a predetermined number of revolutions in the forward direction to draw a certain volume of fluid into the intake nozzle 16 and then produces another contact closure which provides a signal to the stop input terminal 134 of the pump motor control 120 and to the on terminal 136 of the packaging system motor control 124 when the pump has rotated a predetermined number of revolutions in the reverse direction to clear the intake hose 30.

The packaging system motor control 124 includes a switching arrangement having an on position in which it applies power to the packaging system motor 100 to move the packaging system 22 into a position in which it is switched by a signal to its on terminal 136 from the counter 104. This counter 104 counts signals from the pump drive switch 122 indicating a predetermined number or amount of samples or sample have been drawn and applied to a container. The packaging system motor control 124 is switched to its position by a signal applied to its input terminal 136 in which position it causes the rotation of the packaging system motor 100 to seal a package in the packaging system 22. To generate the signal that is applied to the off terminal 138 of the packaging system motor control 124, the packaging system drive switch 128, which may be a cam-operated switch, is positioned to be depressed each time the packaging system 22 completes a container to start preparation for the next container.

With this arrangement, the interval timer 102 in the computer 14 (FIGS. 1 and 8) energizes the pump motor control 120 which energizes the pump assembly 12 to draw a sample as measured by the pump drive switch 122. At the end of drawing the sample, the pump drive switch 122 applies the signal to the counter 104 which resets the pump motor control 120 for the next interval and stops the pump motor by applying a signal to the control 134. This signal is also applied to the counter 104 which counts a predetermined number of counts and then applies a signal to the packaging system motor control 124 indicating the container is full and initiating motion of the packaging system motor 100 to a predetermined position of the packaging system 22 where it hits a switch and turns off the packaging system motor 100 by applying a signal to the off switch 138. The counter 104 is a setable ring counter which may be set to take a predetermined number of samples.

With these embodiments, it is possible to program the computer so that the packages are only nominally filed and thus can receive extra sample without overflow if the pump should pump extra sample because of some irregularity. Similarly, the computer may adjust the size of the package to accommodate different amounts of sample as preprogrammed within the limits of the strength of the bag and may be triggered to pump such extra sample into the bag. The triggering may be caused by a flow meter to increase the size of the bag within limits to draw a sample when the rate of flow or level of liquid has increased indicating that more tests may be desired for the particular package. Similarly, if an event is triggered calling for a larger size sample, multiple packages may be formed if the amount of sample is too large to be held in a single bag with a predetermined strength and the printer caused to label the bags as containing part of the same sample.

Figure 10:
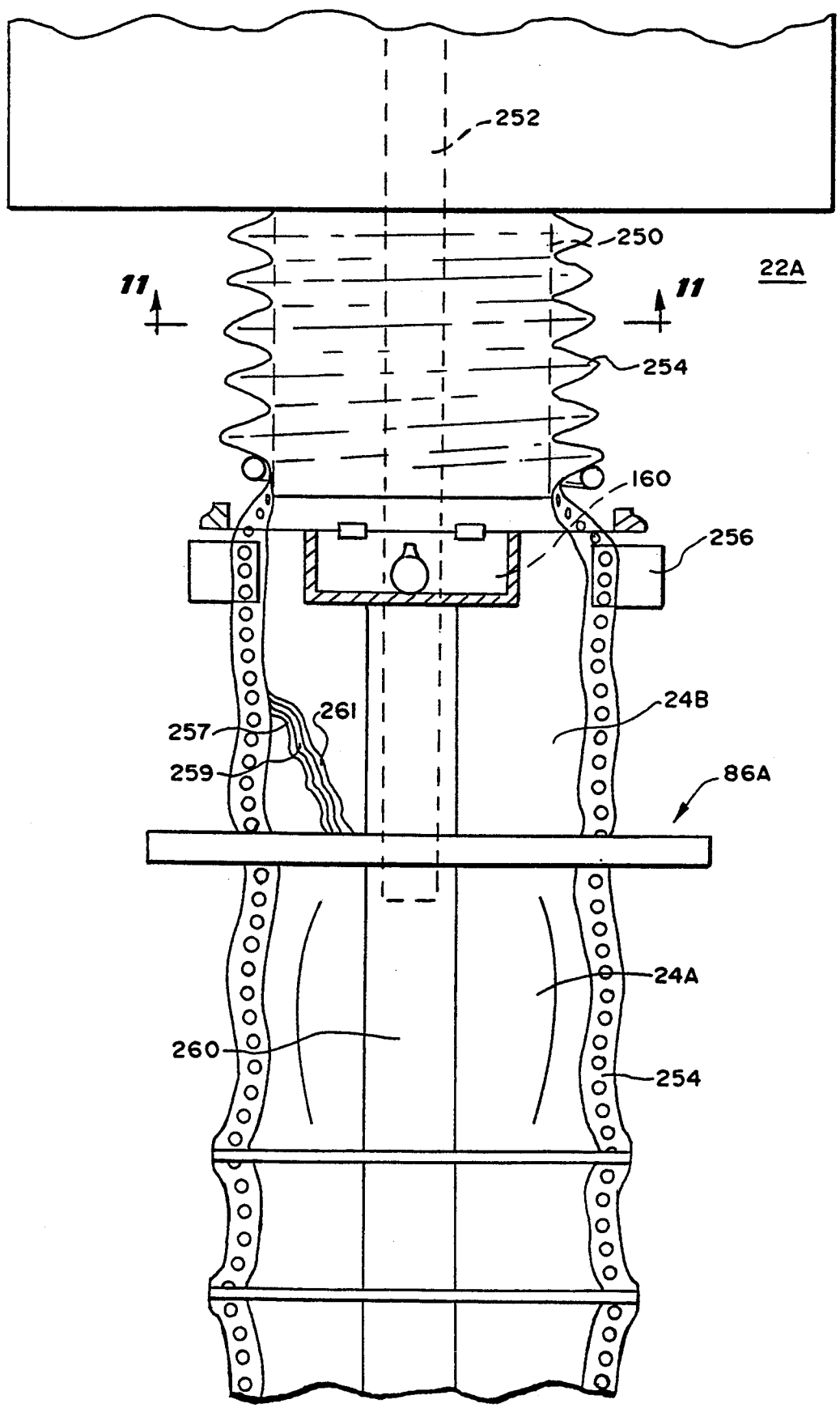
FIG. 10 is a fragmentary, elevational view of another embodiment of web processing system that may be used in the embodiment of FIG. 1 instead of the embodiment of FIG. 4.

In FIG. 10, there is shown an elevational view of another embodiment 22A of web processing system which may be used in the embodiment of FIG. 1 instead of the web processing system 22. In this embodiment, the web processing system 22A includes a mandrel 250, a discharge tube 252, a web material 254, a tractor feed 256 and a heat seal and clamping mechanism 86A. The mandrel 250 receives the discharge tube 252 which extends through the mendrel 250 from the source of liquid and downwardly into the center of the web 254 which is formed as a tube compressed around the outside of the mandrel 250 and the tractor feed engages the web at a lower portion of the mandrel 250. The heat seal mechanism is positioned below the mandrel in a manner similar to the embodiment 22 at an adjustable location to control the size of the sample bag formed and seal it.

In operation, the tractor feed mechanism 256 pulls the web material 252 under computer control downwardly where it is clamped by the clamping mechanism 86A and heat sealed. A bottom heat seal is first formed, the web material pulled further down and liquid inserted through the discharge tube 252. After the required amount of sample or samples is inserted for one package, the top is sealed by the heat seal mechanism 86A.

Preferably, a small portion of web 254 is pulled downwardly and another seal made for the bottom of another sample container. This sample container is filled in the same manner as the previous one to form a sequence of sample packages illustrated as 24A and 24B. A printing mechanism 160 prints on the unfilled web 254 in a manner similar to that of the embodiments of FIGS. 1-9.

In the embodiment of FIG. 10, the web 254 is manufactured from elongated sheets that face each other with the long parallel edges overlapping and sealed to form a tube. The seal is inset from the outer edges and parallel to them so as to form two flat parallel strips extending beyond the parallel inner seals of the tube. The flat parallel strips are formed of overlapping sheets on diametrically opposite sides of the tube, having double the thickness of the walls of the tube. perforations are formed along each the stips in a line so they can be gripped by the tractor feed mechanism 256 to feed the web material. In the alternative, a simple extruded tube may be formed without the parallel strips and the perforations and it may be pulled downwardly in the manner described in connection with the embodiment of FIGS. 1–9.

In the embodiment of FIG. 10, the tubular material is multilayered, having an inner inert layer 257 with other layers added to it for the purpose of protection an sealing and in some cases printing. For example, the inner layer 257 may be polytetrafluoroethylene such as that sold by E. I. DuPont Corporation, Wilmington, Del., under the trademark, Teflon, an adjacent sealing or backing layer 259 may be of polyethylene, a layer 261 may be added for outer abrassion resistance, such as a layer of mylar and a still further layer such as indicated at 260 may be added to receive the printed indicia applied by the printer 160. In some embodiments, the bag may be evacuated of air after receiving a liquid sample by applying suction to the discharge tube 252 prior to sealing.

Figure 11:
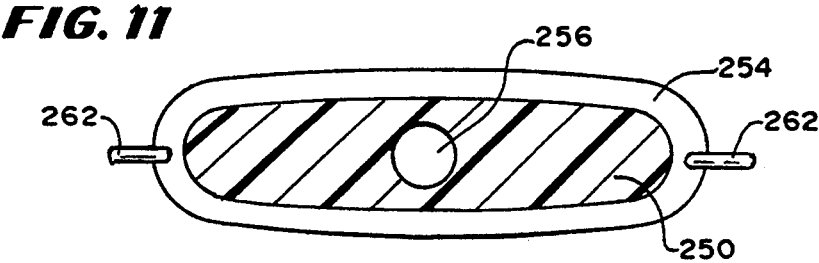
FIG. 11 is a sectional view taken through lines 11—11 of FIG. 10.

In FIG. 11, there is shown a sectional view taken through lines 11—11 showing the discharge tube 252 extending through a plastic eliptical or oblong-shaped mandrel 250 which receives the webbing material 254 and is adapted to have pins 262 of the tractor mechanism 256 (FIG. 10) engage therewith. The mandrel 250 in the preferred embodiment is oblong or eliptical in cross-section as to maintain the web material 254 relatively flat with the perforated edges extending in line with the major axis of the elipse formed by the mandrel 250 and to provide a relatively flat printing surface.

Figure 12:
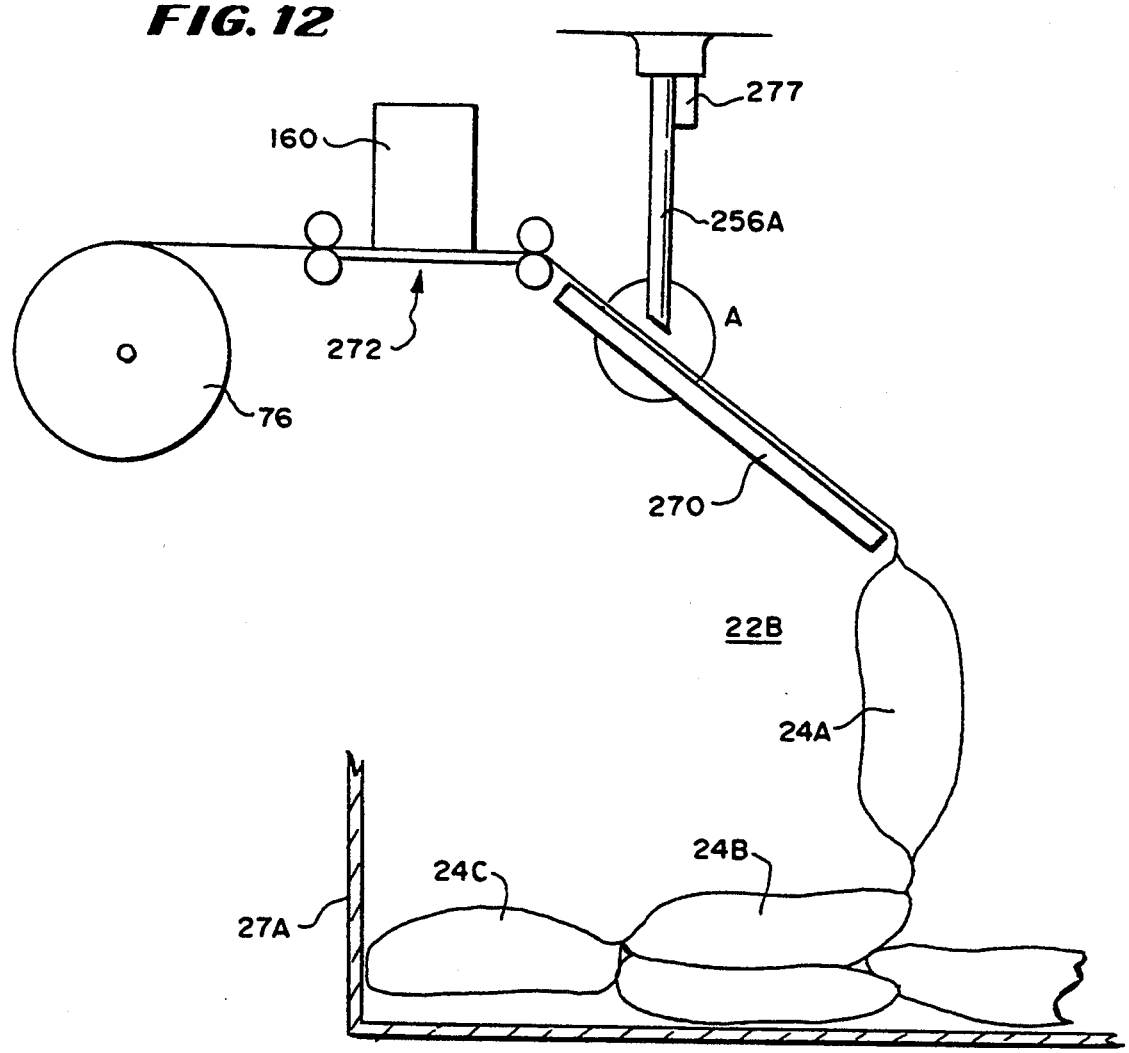
FIG. 12 is a schematic view of still another embodiment of web processing system useable instead of the embodiment of FIG. 10.

In FIG. 12, there is shown still another embodiment 22B of web processing system having the web roll 76, printing mechanism 160, discharge tube assembly 256A compartment 27A for sample packages such as 24A, 24B, 24C, a fill platform 270 and a web control roller assembly 272. The fill platform is angled and located under the dischage tube assembly 256A and the printing assembly 160 is above the web control roller assembly that controls the motion of the web under the control of the microprocessor and holds the web flat for printing.

In this embodiment, the web material is preformed as a plurality of attached bags in a manner known in the art and wound around the web roll 76. It may be pulled downwardly in a manner similar to the embodiments of FIG. 1 or gravity may be relied upon to pull it downwardly under the control of the web control roller assembly which holds the web between rollers and releases it by rotation of the rollers. The sample bags are pulled over the filling platform 270 by gravity and by the web control roller assembly 272 which also pulls the webbing material past the printing mechanism 160 for imprinting thereon.

The discharge tube assembly 256A includes a stinger on the bottom adapted to engage a septum in the sample bags, and a drive pinion and rack assembly 277 controlled in position by a LVDT (linear variable-differential transformer). The dischage tube assembly 256A extends downwardly so that its stinger moves into a septum in the bag but is short of the bottom layer of the bag. The stinger enters the septum and frictionally grasps it when it is in its lowest position.

After the stinger enters the septum, the discharge tube and stinger pulls upwardly to lift the septum and upper wall of the bag a short distance. The pumping mechanism then pumps liquid into the bag and fills it with the programmed amount of sample. Bags already filled, such as 24A, 24B and the like, when released by the rollers of the roller assembly 272 to permit forward movement, pull the bags downwardly after they are filled.

When filled to the programmed extent, the stinger is withdrawn and the septum is snaps closed, after which, the program controlled roller mechanism 272 permits another bag to roll into position under the discharge tube assembly 256A.

Figure 13:
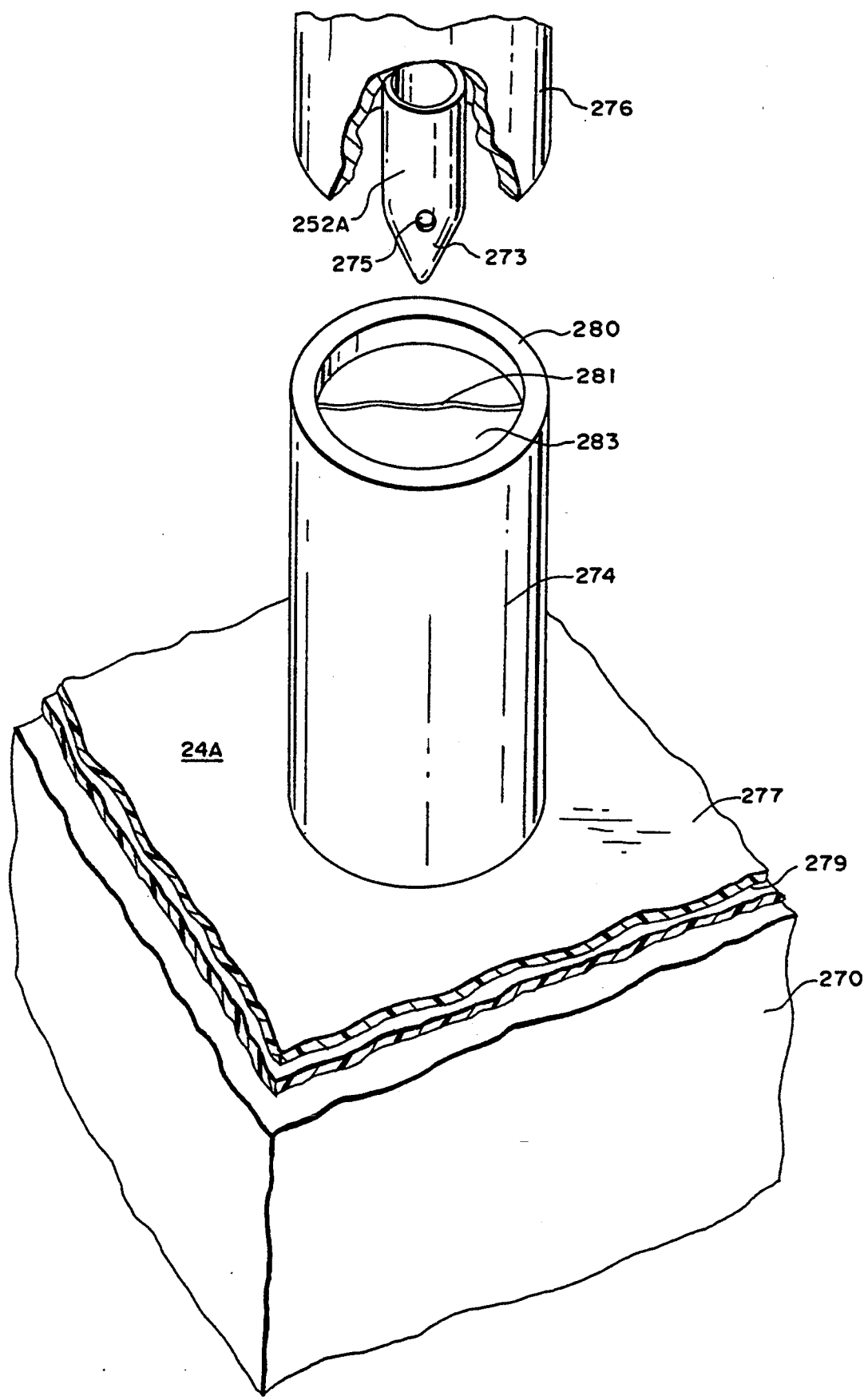
FIG. 13 is a fragmentary enlarged, elevational view, partly broken away of a portion of the embodiment of FIG. 11.

In FIG. 13, there is shown an enlarged, fragmentary view, partly broken away of the discharge tube assembly 256A and the septum 274 forming a portion of the bags, such as 24A, prior to the time they are filled. As shown in this view, the discharge tube assembly 256A includes an outer tubular sheath 276 large enough to rest on the outer wall of the septum 274 and receiving in its interior a tappered inner discharge needle 252A having a pointed end at 273 and a dischage port 275. The discharge needle 252A is aligned to pierce the inner membrane 283 of the septum 274 at 281 so that the port 275 extends below the membrane 283 to inject liquid therein.

The membrane 283 grips the needle 252A frictionally with the bottom of the outer sheath 276 resting on the top edge 280 of the septum. Because of the frictional grip of the septum, the entire outer sheath 276 and needle 273 are slightly raised before liquid flows into the bag to lift the top member 277 of the bag 24A from the bottom member 279 to permit the flow of liquid.

The fluid is discharged between the two layers of the bag while it rests on the roller platform 270. After the bag is filled, the inner discharge needle 273 is pulled upwardly, releasing the frictional grip on the septum and permitting the septum to close into a liquid tight seal in a manner known in the art. Since the frictional grip has been released, the bag such as 24A (FIG. 12) is now free to move when released by the roller mechanism 272 (FIG. 12) under its own weight. The entire discharge tube assembly may be pulled slightly updwardly at the time or before the release of the bags by the mechanism 272 to permit the bag, without interference, to be pulled downwardly by the weight of previous bags and by its own weight on the platform 270.

The discharge needle 273 should be made of an inert material such as stainless steel and have a diameter of at least 0.125 of an inch to permit sufficient flow of liquid into the bagging material. The septum 274 will be of corresponding size such as at least 0.375 of an inch.

In FIG. 14, there is shown another embodiment of web processing system 22C having a discharge tube assembly 290 and a preformed flexible bag assembly 292. The preformed bag assembly 292 supports a plurality of preformed bags such as 24A, 24B and the like, each of which has a corresponding septum 274A, 274B and the like, movably on a holder assembly 294 with their corresponding septa extending upwardly in a first direction facing the discharge tube assembly 290.

The discharge tube assembly 290 grasps the preformed bags, one by one, and moves them one by one sequentially along the holder assembly 294 into a first position in which indicia may be imprinted upon them and then to a second position in which they may be filled, prior to being dropped into a container.

The preformed bag assembly 292 includes a bag support system 294, the printing assembly 160 and a support plateform 296. The bag support system 294 includes parallel pairs of rails, with each rail passing through a corresponding one of two eyelets on each of the bags 24A–24G. The bags 24A–24G each have a corresponding one of the septums 274A–274G extending upwardly beyond the support system 294 for engagement with the dischage tube assembly 290.

To temporarily support the empty bags on a flat surface for printing of indicia, the horizontal flat support platform 296 is positioned in the path of a movable print mechanism 160 and under the bag support system 294. The bag support system ends at a container into which filled bags are deposited.

In this embodiment, the discharge tube assembly 290 engages the septums one by one, such as the septums 274A-274G, and moves the septums along the support means 294 so that the corresponding one of the bags 24A-24G lies flat on the support surface 296. The printhead 160 is then moved over the bag and the support mechanism 296 to print the required indicia. After the printing, the discharge assembly 290 moves each the bag further to a position where it drops free of the support surface 296, at which time it is filled and the discharge mechanism 290 moves it free from the support system 294.

The discharge assembly 290 includes an outer tubular sheath 276, an inner needle 273 and a downwardly, vertically-moving control assembly 277 that operates in the same manner as the embodiment of FIGS. 12 and 13. The discharge needle 273 communicates with an inner telescoping tube 300 which is moved by a motorized rack and pinion system 302 to reciprocate along the bag holding assembly 294 to move the bags one by one into position. The positioning mechanism is encoded on a code wheel on the motor 302 which moves the rack to position the discharge needle 273 under the control of the microprocessor 14. Instead of moving the bags from position to position on the bag holding assembly 294, the bags may remain in place and the telescoping tube 300 may move the discharge needle 273 over each bag and fill them in place without moving them.

For this purpose, the microprocessor 14 receives signals indicating the first position for engaging the septum while the bag is on the support 296, a second position for printing, a third position for filling the bag after it has fallen from the support 296 and a fourth position at the end of its travel path, at which time the bags, already filled, are pushed free of the support 294 to drop into a container located nearby.

In FIG. 15, there is shown a plan view of the support system 294 having first and second parallel rails 310 and 312 upon which the bags 24A-24C are mounted through eyelets in the ends of the bags so that the bags depend downwardly from the rails. With this arrangement, the bags 24A-24C are stretched between the rails 310 and 312 so they are relatively flat with their septums 274A-274C extending upwardly between the rails.

As shown in FIG. 14, the septum of each bag may be grasped by the discharge assembly 290 one by one and the bags moved over the support surface 296. While there, the printing mechanism 160 is moved on parallel shafts 314 and 316 so that it is cantalevered over the bag and the support 296. The printhead is driven by a nut and screw drive, with the shaft 314 rotably positioning it. The motor drive for the shaft 314 includes a coded wheel which positions the printhead and controls the timing of its position with the indicia under the control of the microprocessor.

In FIG. 16, there is shown a block diagram of the sampler 10 interconnected with a flow meter 320 and/or a liquid level detector 322 positioned in a liquid flow path 324. These instruments detect either the flow rate or the liquid level and provide a signal to the microprocessor 14 which controls the printing of the sample information on the bag and the collection of the sample by the sampler 10, indicating the condition that results in the taking of a sample. For example, the liquid height or a sudden increase in the flow rate may indicate the proper time for taking a sample or for taking a larger sample. In that event, the time and the reason for sampling are printed on the bag.

From the above description, it can be understood that the wastewater sampler of this invention has several advantages such as: (1) it can form a large number of packages; (2) data is conveniently printed right on the package as it is formed; (3) the size of the package can be automatically tailored to the size of the sample to avoid air that may contaminate the liquid therein; (4) the sample is immediately sealed in the package amd thus reduces contamination; and (5) overflow can easily be avoided.

Although a specific embodiment has been described with some particularity, many modifications and variations may be made in this specific embodiment without deviating from the invention. Therefore, it is to be understood that, within the scope of the appended claims, the invention may be practiced other than as specifically described.

What is claimed is:

1. A sampler comprising:

an inlet port adapted to communicate with a source of water and an outlet port positioned so that water flows from the inlet port to the outlet port;

means for pumping fluid through the inlet port for collection;

means for initiating movement of a web of packaging material;

means for folding the web of packaging material and sealing it to form a pouch;

means for causing water from the inlet port to flow from the outlet port into the pouch;

means for sealing the pouch;

means for controlling the pumping means; and means for drawing the web so that the pouch corresponds in internal volume to the volume of water pumped into the pouch prior to sealing the pouch.

2. A sampler comprising:

an inlet port adapted to communicate with a source of water and an outlet port positioned so that water flows from the inlet port to the outlet port;

means for pumping fluid through the inlet port for collection;

means for initiating movement of a web of packaging material formed into bags;

means for causing water from the inlet port to flow from the outlet port into the bags;

means for sealing the bags; and programmable means for controlling the means for pumping and means for initiating movement of a web so that each of the bags corresponds in internal volume to the volume of water pumped into the bag prior to sealing the bag.

3. A sampler in accordance with claim 2 in which the means for forming the bag includes a means for folding the web against itself and heat-sealing the web together, whereby a bag is formed before the water is inserted, and sealing the web to form a water-tight container.

4. A water sampler in accordance with claim 3 further including means for printing information on the web.

5. A sampler in accordance with claim 1 in which the means for forming the pouch includes a means for folding the web against itself and heat-sealing the web together, whereby a pouch is formed before the water is inserted and sealing it to form a water-tight container.

6. A method of sampling water, comprising the steps of:
   causing the water to flow from an inlet port and an outlet port;
   periodically taking samples of the water;
   pulling a web from a reel at a time related to the drawing of samples;
   forming a container with an open top from the web material;
   pumping at least one sample into the container;
   sealing the container; and
   storing the container in a housing, wherein a larger number of samples may be taken and stored in the housing before being taken to a laboratory for testing than if the containers were rigid.

7. A method in accordance with claim 6 in which the containers remain connected together as they are filled with a sample.

8. A method according to claim 7 in which the web material out of which the container is formed has identification printed upon it.

9. A method according to claim 8 in which the identification includes the time of taking the sample.

10. A method in accordance with claim 9 in which the identification on the container includes the location from which the sample was taken.

11. A method in accordance with claim 10 in which the amount of the sample is controlled and the size of the container controlled so that the volume of the container corresponds with that of the sample.

12. A method of sampling water, comprising the steps of:
   causing the water to flow from an inlet port and an outlet port;
   periodically taking samples of the water;
   moving flexible containers and the outlet port with respect to each other one by one into a filling position;
   pumping at least one sample into at least some of the flexible containers;
   sealing the flexible containers;
   accumulating filled containers in a housing; and
   taking a large number of the accumulated filled containers to a laboratory to test the samples.

13. A method in accordance with claim 12 in which the containers remain connected together as they are filled with a sample.

14. A method according to claim 13 in which the web material out of which the container is formed has identification printed upon it.

15. A method according to claim 14 in which the identification includes the time of taking the sample.

16. A method in accordance with claim 15 in which the identification on the container includes the location, from which the sample was taken.

17. A method in accordance with claim 16 in which the amount of the sample is controlled and the size of the container controlled so that the volume of the container corresponds with that of the sample.

18. A sampler, comprising:
   an inlet port adapted to communicate with a source of water and an outlet port positioned so that water flows from the inlet port to the outlet port;
   means for pumping fluid through the inlet port for collection;
   means for initiating movement of a web of packaging material;
   means for folding the web of packaging material and sealing it to form a pouch;
   means for causing water from the inlet port to flow from the outlet port into the pouch;
   means for sealing the pouch; and
   programmable means for controlling the pumping means and means for initiating movement of a web so that a sample is drawn and inserted into the pouch at programmed increments of the flow of water past a point in the source of water as indicated by a flow meter.

19. A sampler, comprising:
   an inlet port adapted to communicate with a source of water and an outlet port positioned so that water flows from the inlet port to the outlet port;
   means for pumping fluid through the inlet port for collection;
   means for initiating movement of a web of packaging material;
   means for folding the web of packaging material and sealing it to form a pouch;
   means for causing water from the inlet port to flow from the outlet port into the pouch;
   means for sealing the pouch; and
   programmable means for controlling the pumping means and means for initiating movement of a web so that a sample is drawn and inserted into the pouch at programmed time periods.

20. A sampler, comprising:
   an inlet port adapted to communicate with a source of water and an outlet port positioned so that water flows from the inlet port to the outlet port;
   means for pumping fluid through the inlet port for collection;
   means for initiating movement of a web of packaging material;
   means for folding the web of packaging material and sealing it to form a pouch;
   means for causing water from the inlet port to flow from the outlet port into the pouch;
   means for sealing the pouch; and
   programmable means for controlling the pumping means and means for initiating movement of a web so that a sample is drawn and inserted into the pouch at programmed water levels of the source of water as indicated by a water level sensor.

* * * * *